United States Patent
Seo et al.

(10) Patent No.: US 10,006,872 B2
(45) Date of Patent: Jun. 26, 2018

(54) OPTICAL INSPECTION SYSTEM

(71) Applicants: Samsung Electronics Co., Ltd., Suwon-si, Gyeonggi-do (KR); Samsung Display Co., Ltd., Yongin, Gyeonggi-do (KR)

(72) Inventors: Wonguk Seo, Gunpo-si (KR); Kyoungchon Kim, Goyang-si (KR); Kuihyun Yoon, Seoul (KR); Kyunlae Kim, Suwon-si (KR); Jaeyoung Park, Hwaseong-si (KR); Kyoungho Yang, Hwaseong-si (KR); Young Heo, Osan-si (KR)

(73) Assignee: Samsung Electronics Co., Ltd. (KR)

(*) Notice: Subject to any disclaimer, the term of this patent is extended or adjusted under 35 U.S.C. 154(b) by 247 days.

(21) Appl. No.: 14/955,331

(22) Filed: Dec. 1, 2015

(65) Prior Publication Data
US 2016/0290933 A1    Oct. 6, 2016

(30) Foreign Application Priority Data
Mar. 31, 2015    (KR) .................. 10-2015-0045396

(51) Int. Cl.
| | | |
|---|---|---|
| *G01N 21/958* | (2006.01) | |
| *G01N 21/88* | (2006.01) | |
| *G01N 21/94* | (2006.01) | |
| *G01N 21/95* | (2006.01) | |

(52) U.S. Cl.
CPC ......... *G01N 21/94* (2013.01); *G01N 21/8806* (2013.01); *G01N 21/958* (2013.01); *G01N 2021/9513* (2013.01)

(58) Field of Classification Search
CPC ............................ G01N 21/94; G01N 21/958
USPC .......................................... 356/237.1–237.6
See application file for complete search history.

(56) References Cited

U.S. PATENT DOCUMENTS

| | | | |
|---|---|---|---|
| 4,575,399 A | 3/1986 | Tanaka et al. | |
| 4,893,932 A | 1/1990 | Knollenberg | |
| 5,604,134 A * | 2/1997 | Chang | ............. H01L 22/12 |
| | | | 257/E21.53 |

(Continued)

FOREIGN PATENT DOCUMENTS

| | | |
|---|---|---|
| JP | 05-006929 | 1/1993 |
| JP | 05-264440 | 10/1993 |

(Continued)

*Primary Examiner* — Hina F Ayub
*Assistant Examiner* — Amanda Merlino
(74) *Attorney, Agent, or Firm* — Myers Bigel, P.A.

(57) ABSTRACT

Provided is an optical inspection system including a supporting unit, allowing a target object to be loaded thereon, a light source unit configured to emit a laser beam toward the target object, a light condensing unit collecting scattered light that is scattered at the target object when the laser beam is irradiated onto the target object, and a control unit controlling the light source unit and the light condensing unit and analyzing the scattered light to examine whether there are pollutants on the target object. The supporting unit may include a first supporting unit, on which the target object is disposed, and which is formed of a first material, and a second supporting unit, which is disposed under the first supporting unit and is formed of a second material different from the first material.

17 Claims, 12 Drawing Sheets

(56) References Cited

U.S. PATENT DOCUMENTS

| | | | | |
|---|---|---|---|---|
| 6,046,802 | A * | 4/2000 | Ortiz, Jr. | G01N 21/958 |
| | | | | 356/237.1 |
| 6,236,056 | B1 * | 5/2001 | Moriya | G01N 21/94 |
| | | | | 250/559.4 |
| 6,836,322 | B2 | 12/2004 | Bae | |
| 7,714,996 | B2 | 5/2010 | Yan et al. | |
| 8,027,036 | B2 | 9/2011 | Kim et al. | |
| 8,673,656 | B2 | 3/2014 | Yves | |
| 2009/0284736 | A1 * | 11/2009 | Tosi | G01R 31/311 |
| | | | | 356/237.2 |
| 2013/0038866 | A1 * | 2/2013 | Kren | H01L 21/68735 |
| | | | | 356/237.5 |
| 2013/0114880 | A1 | 5/2013 | Matsumoto et al. | |

FOREIGN PATENT DOCUMENTS

| | | |
|---|---|---|
| JP | 2002-195959 | 7/2002 |
| JP | 2010-045146 | 2/2010 |
| KR | 10-0333613 | 4/2002 |
| KR | 10-2003-0092803 | 12/2003 |
| KR | 10-0657665 | 12/2006 |
| KR | 10-0989216 | 10/2010 |
| KR | 20-2011-001795 U | 2/2011 |
| KR | 10-1338308 | 12/2013 |

\* cited by examiner

OPTICAL INSPECTION SYSTEM

CROSS-REFERENCE TO RELATED APPLICATIONS

This U.S. non-provisional patent application claims priority under 35 U.S.C. § 119 to Korean Patent Application No. 10-2015-0045396, filed Mar. 31, 2015, in the Korean Intellectual Property Office, the entire contents of which are hereby incorporated herein by reference.

FIELD

Example embodiments of the inventive concept provide an optical inspection system, and in particular, an optical inspection system configured to perform a pollutant detection process on a substrate for a flat panel display device.

BACKGROUND

As a result of an advance in information communication technologies and various demands of an information-oriented society, there is an increasing demand for display devices, and flat panel display (FPD) devices are being widely used. For example, an electroluminiscent display device (ELD) device, a liquid crystal display device (LCD) (e.g., a TFT-LCD or TN/STN) device, a plasma display panel device, and an organic EL device are being used as flat panel display devices. To stably control product quality of flat panel display devices, it is conventional to detect defects and remove them from fabricated flat panel display devices. For example, when pollutants remain on a flat panel display device, they may lead to defects, such as bright dot, dark dot, hot pixel, dead pixel, or the like. The defect sources on a flat panel display device can be examined by an optical inspection process. For example, a laser beam can be used for such an optical inspection process. However, in the case where a display substrate may allow the laser beam to penetrate therethrough, the laser beam may be scattered by a substrate supporting structure disposed under the display substrate. A thin film may be coated on the display substrate to reduce optical transmittance of the display substrate, but it may be difficult to prevent the laser beam from passing through the display substrate. In other words, there may be difficulty in preventing the laser beam from being scattered by the substrate supporting structure. In the case where the optical inspection process is performed using light scattered by the display substrate, light scattered by the substrate supporting structure may serve as a noise factor in the optical inspection process, thereby causing deterioration in image quality and in inspection reliability of the optical inspection process.

SUMMARY

Example embodiments of the inventive concept provide a highly-reliable optical inspection system and an optical inspection method using the same.

According to example embodiments of the inventive concept, an optical inspection system may include a supporting unit, allowing a target object to be loaded thereon, a light source unit configured to emit a laser beam toward the target object, a light condensing unit collecting scattered light that is scattered at the target object when the laser beam is irradiated onto the target object, and a control unit controlling the light source unit and the light condensing unit and analyzing the scattered light to examine whether there are pollutants on the target object. The supporting unit may include a first supporting unit, on which the target object is disposed, and which is formed of a first material, and a second supporting unit, which is disposed under the first supporting unit and is formed of a second material different from the first material.

In example embodiments, the first material may have higher transmittance than the second material.

In example embodiments, the second material may have higher reflectance than the first material.

In example embodiments, the transmittance of the first material may be 90% or higher.

In example embodiments, the second material may be a metal layer, which is treated to have a mirror effect.

In example embodiments, the control unit may be configured to control a position of the light source unit in such a way that an incidence angle of the laser beam ranges from about 70° to about 80°.

In example embodiments, the light source unit may be configured to generate an s-polarized laser beam.

In example embodiments, the first supporting unit may be provided to have at least one recessed region whose bottom surface is lower than a top surface of the first supporting unit.

In example embodiments, the recessed region may have a side surface continuously connected to the top surface of the supporting unit, thereby having a rounded profile.

In example embodiments, the light source unit may further include a refraction plate, allowing for a change in irradiation position of the laser beam.

In example embodiments, the target object may include at least one thin-film transistor.

BRIEF DESCRIPTION OF THE DRAWINGS

Example embodiments will be more clearly understood from the following brief description taken in conjunction with the accompanying drawings. The accompanying drawings represent non-limiting, example embodiments as described herein.

Figure 1:
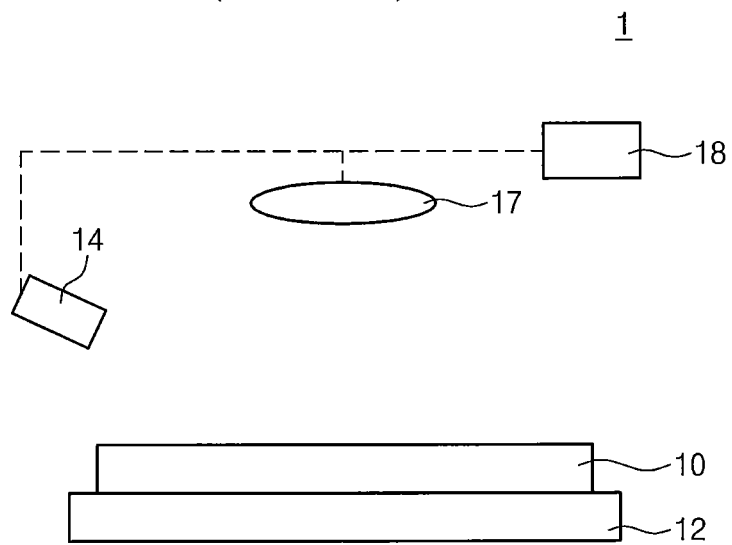
FIG. 1 is a schematic diagram illustrating a conventional optical inspection system.

It should be noted that these figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION

Example embodiments of the inventive concepts will now be described more fully with reference to the accompanying drawings, in which example embodiments are shown. Example embodiments of the inventive concepts may, however, be embodied in many different forms and should not be construed as being limited to the embodiments set forth herein; rather, these embodiments are provided so that this disclosure will be thorough and complete, and will fully convey the concept of example embodiments to those of ordinary skill in the art. In the drawings, the thicknesses of layers and regions are exaggerated for clarity. Like reference numerals in the drawings denote like elements, and thus their description will be omitted.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers indicate like elements throughout. As used herein the term "and/or" includes any and all combinations of one or more of the associated listed items. Other words used to describe the relationship between elements or layers should be interpreted in a like fashion (e.g., "between" versus "directly between," "adjacent" versus "directly adjacent," "on" versus "directly on").

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments of the inventive concepts belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

An optical inspection system is configured to optically inspect a target object 10. Here, the target object 10 may be a transparent substrate. The target object 10 may be configured to allow a laser beam to pass therethrough with high transmittance. For example, the target object 10 may include or be a glass substrate, which may be usually used for flat panel display devices. As an example, the target object 10 may be a substrate for liquid crystal display (LCD), plasma display panel (PDP), electroluminescent display (ELD), vacuum fluorescent display (VFD), or the like. In the case where the target object 10 is provided in the form of a transparent substrate, it may have high transmittance with respect to a laser beam, compared with a semiconductor wafer. The optical inspection system may be a dark field (DF) inspection system configured to detect defects, which may occur on the target object 10. The target object 10 may be configured to include thin-film transistors (TFTs). Hereinafter, in the drawings, an arrow may represent light flow along a direction of the arrow.

FIG. 1 is a schematic diagram illustrating a conventional optical inspection system 1. Referring to FIG. 1, the optical inspection system 1 may include a supporting unit 12, a light source unit 14, a light condensing unit 17, and a control unit 18. The target object 10 may be disposed on the supporting unit 12.

The light source unit 14 may be configured to irradiate a laser beam onto the target object 10. The light condensing unit 17 may be configured to collect a fraction (hereinafter, scattered light) of the irradiated laser beam scattered from the target object 10. The light condensing unit 17 may be positioned over an inspection region, which is a part of the target object 10. The light condensing unit 17 may be provided to be perpendicular to a normal line of a surface, on which the target object 10 is disposed. The light condensing unit 17 may be configured to transmit information on the scattered light to the control unit 18. The control unit 18 may be configured to control the light source unit 14 and the light condensing unit 17. The control unit 18 may be configured to control process parameters (e.g., positions, operation times, operation sequences, or the like) associated with the light source unit 14 and the light condensing unit 17. The control unit 18 may be configured to analyze light scattered from the target object 10 (i.e., the scattered light) and detect whether there is a pollutant on the target object 10. Furthermore, the control unit 18 may be configured to analyze the size of pollutants on the target object 10.

FIGS. 2A through 2D are schematic diagrams sequentially illustrating an optical inspection process using the optical inspection system 1 of FIG. 1.

Figure 2A:
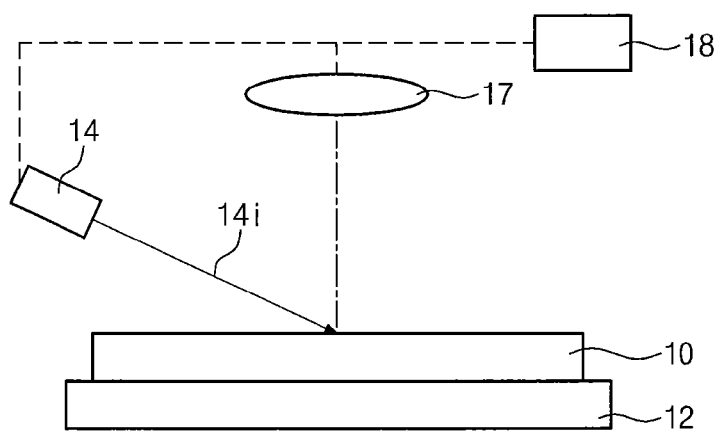
FIGS. 2A through 2D are schematic diagrams sequentially illustrating an optical inspection process using the optical inspection system of FIG. 1.

Referring to FIG. 2A, the light source unit 14 may be configured to emit incident light 14*i* toward the target object 10 disposed on the supporting unit 12. The incident light 14*i* may be generated in the form of a laser beam. In example embodiments, the light source unit 14 may be configured to generate a high-power laser beam.

Figure 2B:
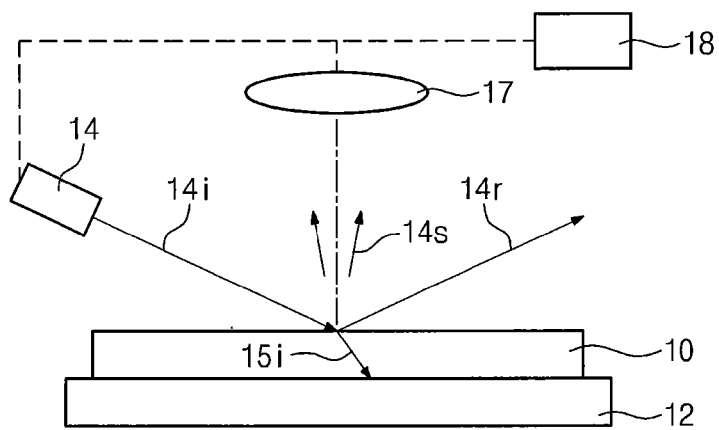

Referring to FIG. 2B, if the incident light 14*i* is irradiated on the target object 10, a fraction of the incident light 14*i* may be reflected from the target object 10 to form reflected light 14*r*. Here, another fraction of the incident light 14*i* may be firstly scattered by the target object 10 to form first scattered light 14*s*. The light condensing unit 17 may be configured to collect the first scattered light 14*s* and transmit image information obtained from the first scattered light 14*s* to the control unit 18. In the control unit 18, the image information may be used to detect whether there is a pollutant on the target object 10. Furthermore, the control unit 18 may examine sizes and/or positions of pollutants, which may occur on the target object 10. Here, other fraction of the incident light 14*i* may be refracted through the target object 10 to form first refracted light 15*i* propagating into the target object 10.

Figure 2C:
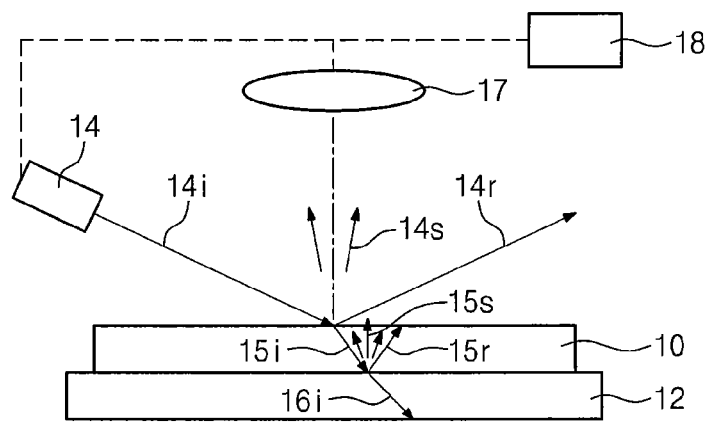

Referring to FIG. 2C, the first refracted light 15*i* may be secondly scattered by a top surface of the supporting unit 12 to form reflected light 15*r* and second scattered light 15*s*. Since the supporting unit 12 is positioned directly under the target object 10, the second scattered light 15*s* may be directly generated from the top surface of the supporting unit 12. Accordingly, the second scattered light 15*s* may be incident into and be detected by the light condensing unit 17 and may serve as a noise factor in detection of pollutants based on the analysis of the first scattered light 14*s*. In addition, a fraction of the first refracted light 15*i* may be refracted through the top surface of the supporting unit 12 to form second refracted light 16*i* propagating into the supporting unit 12.

Figure 2D:
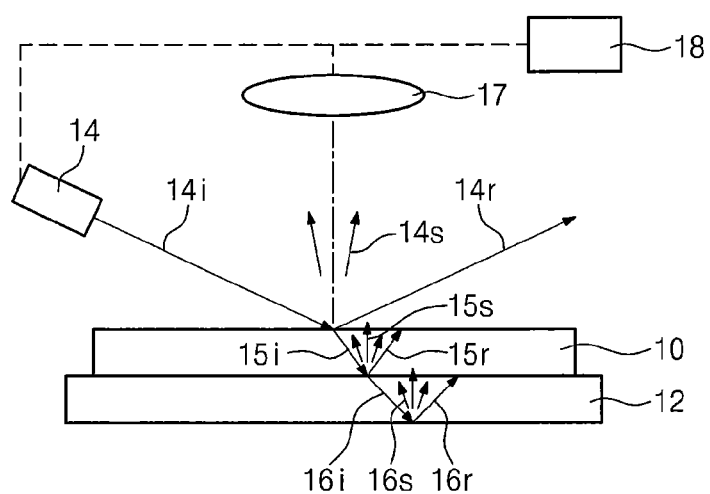

Referring to FIG. 2D, the second refracted light 16*i* may be thirdly scattered by a bottom surface of the supporting unit 12 to form reflected light 16*r* and third scattered light 16*s*. The third scattered light 16*s* may be incident into and be detected by the light condensing unit 17. Accordingly, the third scattered light 16*s* may serve as a noise factor in detection of pollutants based on the analysis of the first scattered light 14*s*.

Referring to FIGS. 1 and 2A through 2D, in the case of using the optical inspection system 1, the second scattered light 15*s* and the third scattered light 16*s* may serve as a noise factor in an optical inspection process based on the first scattered light 14*s*. If more underlying structures are provided below the target object 10, the optical inspection process may suffer from noise caused by additionally scattered light. Since such noise leads to deterioration in reliability of the optical inspection process, it is necessary to reduce the noise in the optical inspection process. In particular, if the size of pollutants on the target object 10 is small, it is necessary to reduce the noise factor or prevent undesired scattering light from being incident into the light condensing unit 17. For example, in the case where the pollutants are nano-sized particles or smaller, a technology capable of more precisely detecting such fine particles is needed for the optical inspection process.

Figure 3:
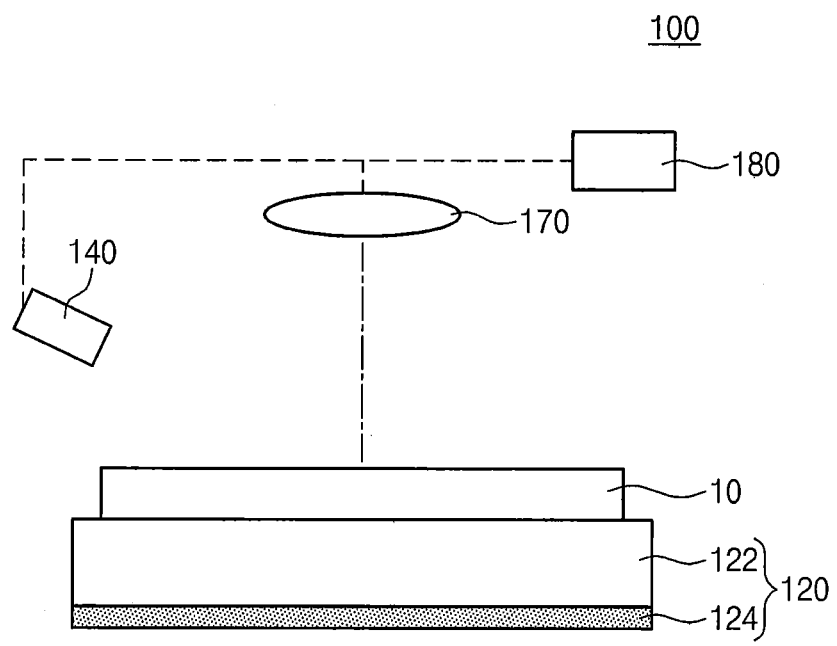
FIG. 3 is a schematic diagram illustrating an optical inspection system according to first embodiments of the inventive concept.

FIG. 3 is a schematic diagram illustrating an optical inspection system 100 according to first embodiments of the inventive concept. The optical inspection system 100 may be a dark field (DF) inspection system configured to detect defects, which may occur on the target object 10. Referring to FIG. 3, the optical inspection system 100 may include a supporting unit 120, a light source unit 140, a light condensing unit 170, and a control unit 180 (e.g., a processor). The target object 10 may be disposed on the supporting unit 120. The target object 10 may be a transparent substrate or a semiconductor substrate. The target object 10 may be configured to include thin-film transistors (TFTs). The target object 10 may be formed of or include one of various materials (e.g., glass).

The supporting unit 120 may include a first supporting member or unit 122 and a second supporting member or unit 124. The target object 10 may be provided on a top surface of the first supporting unit 122. The first supporting unit 122 may be formed of a first material. The second supporting unit 124 may be provided below the first supporting unit 122. The second supporting unit 124 may be provided to face the first supporting unit 122. The second supporting unit 124 may be provided to have substantially the same size and shape as the first supporting unit 122. However, in certain embodiments, the size and shape of the second supporting unit 124 may be changed in various manners. Optionally, the second supporting unit 124 may be grounded to prevent a short circuit from being formed. The second supporting unit 124 may be formed of or include a second material different from the first material. The first material may have higher transmittance than that of the second material. For example, the first material may be selected to have transmittance of 90% or higher. Accordingly, most of the incident light irradiated toward the target object 10 may pass through the first supporting unit 122, and thus, it is possible to reduce an amount of noise light to be produced at the top surface of the first supporting unit 122. The second material may be configured to have higher reflectance than that of the first material. For example, the second material may be a metal layer, which is treated to have a mirror effect or a mirror. Accordingly, most of refracted light passing through the first supporting unit 122 may be reflected by the top surface of the second supporting unit 124, and thus, it is possible to reduce an amount of noise light to be produced at the top surface of the second supporting unit 124. By reducing an amount of scattered light at the top surface of the second supporting unit 124, it is possible to reduce the amount of noise light.

The light source unit 140 may be configured to irradiate a laser beam onto the target object 10. In example embodiments, the light source unit 140 may be configured to generate a high-power laser beam. Although the light source unit 140 is illustrated to be a line-shaped light source, it may be provided in various forms (e.g., a dome-shaped light source). The light source unit 140 may be configured to sequentially irradiate laser beams with different wavelengths to the target object 10.

Figure 4:
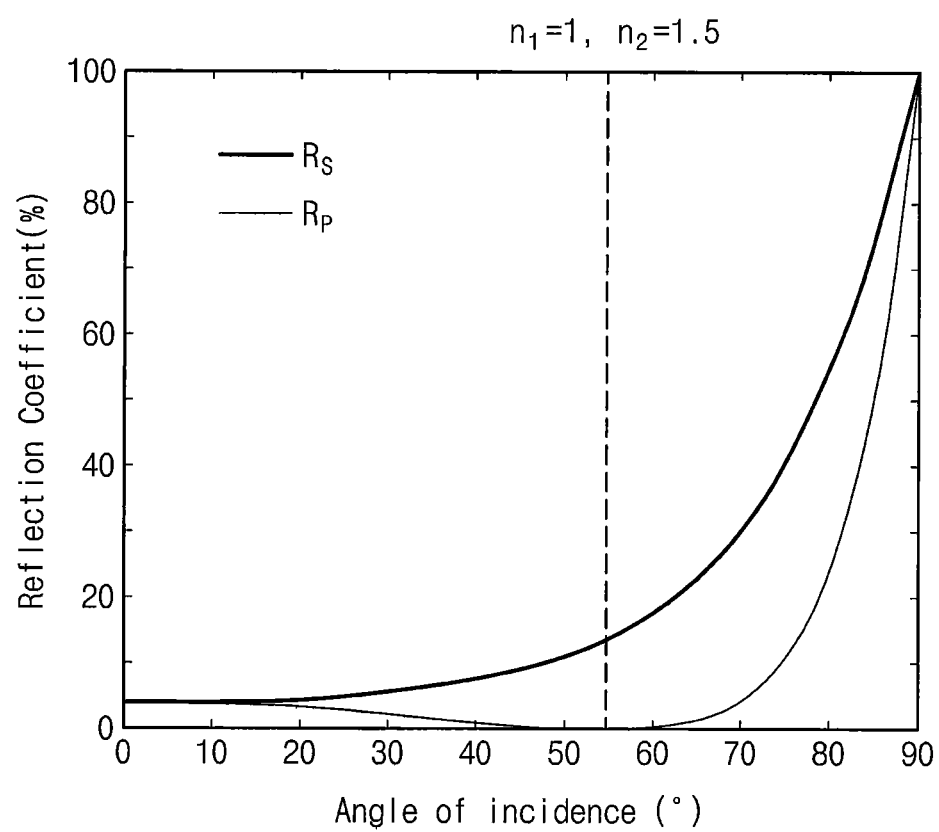
FIG. 4 is a graph illustrating reflection coefficients of s-polarized and p-polarized light according to an angle of incidence.

FIG. 4 is a graph illustrating reflection coefficients of s-polarized and p-polarized light according to an angle of incidence of the incident light. The angle of incidence may be an angle between a normal line to the top surface of the target object 10 and a propagating direction of incident light 140*i* emitted from the light source unit 140 (see FIG. 5A). The incident light 140*i* may be incident from the air, whose refractive index is n1, into a medium, whose refractive index is n2 that is larger than n1. The reflection coefficient may be given by a ratio in amplitude between the incident light and the reflected light, which is a fraction of the incident light reflected from an interface between two media. For example, the reflection coefficient curves of FIG. 4 correspond to light propagating from the air (n1=1) into the target object 10 (n2=1.5). The thick curve represents a reflection coefficient, Rs, of s-polarized light, while the thin curve represents a reflection coefficient, Rp, of p-polarized light. Referring to FIG. 4, when a laser beam is incident from the air onto the target object 10, the reflection coefficient Rs of the s-polarized light is higher than the reflection coefficient Rp of the p-polarized light. The s-polarized light has an electric field oscillating in a direction normal to a plane of incidence, and the p-polarized light has an electric field oscillating in a direction parallel to the plane of incidence. The greater the angle of incidence, the higher the reflection coefficient. This means that, by increasing reflectance of the target object 10, it is possible to decrease transmittance of the laser beam.

Accordingly, the light source unit 140 may be configured to emit s-polarized light. The light source unit 140 may include a polarization member, such as a polarization film or a polarization filter. The angle of incidence may range from 65° to 85°. In example embodiments, the angle of incidence may range from 70° to 80°. This configuration may make it possible to reduce or minimize an intensity of the laser beam propagating toward the supporting unit 120, and consequently, a signal intensity of the scattered light can be controlled to have strong dependence on the presence of pollutants on the target object 10. In certain embodiments, the light source unit 140 may include a light receiving unit located at an opposite position with respect to the normal line of the target object 10.

The light condensing unit 170 may be positioned over an inspection region, which is a part of the target object 10. The light condensing unit 170 may be provided to be perpendicular to a normal line of a surface, on which the target object 10 is disposed. The light condensing unit 170 may be configured to collect light scattered by the target object 10. The light condensing unit 170 may be configured to obtain information of the scattered light and transmit it to the control unit 180. The light condensing unit 170 may be a detection camera configured to receive the scattered light.

The control unit 180 may control the light source unit 140 and the light condensing unit 170. The control unit 180 may be configured to control process parameters (e.g., positions, operation times, operation sequences, or the like) associated with the light source unit 140 and the light condensing unit 170. The control unit 180 may receive the image information from the light condensing unit 170. The control unit 180 may analyze the scattered light transmitted from the target object 10 to analyze whether there are pollutants on the target object 10. The control unit 180 may obtain information associated with attachment or sizes of pollutants, based on comparison of the images taken by the light condensing unit 170. Furthermore, the control unit 180 may provide the image, which may, be generated from the image signals transmitted from the light condensing unit 170, to an operator.

FIGS. 5A through 5D are schematic diagrams sequentially illustrating an optical inspection process using the optical inspection system 100 of FIG. 3.

Figure 5A:
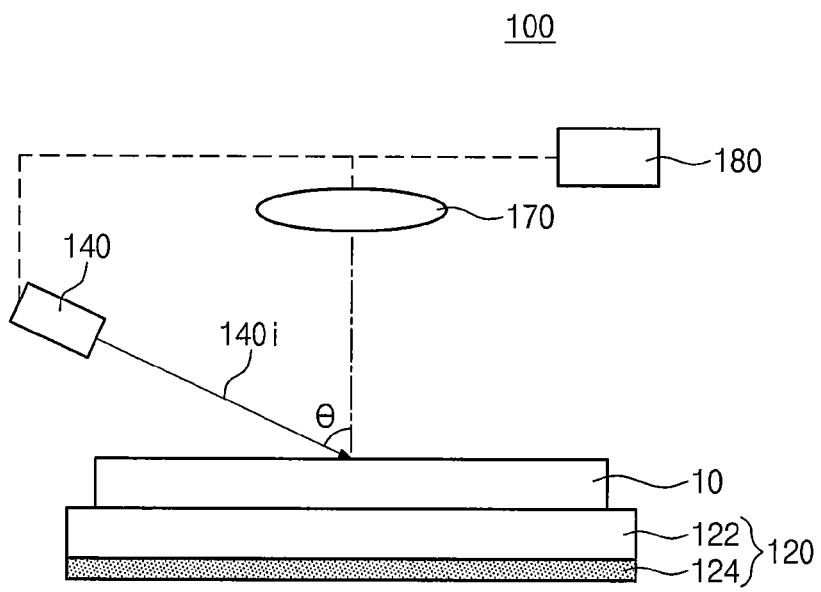
FIGS. 5A through 5D are schematic diagrams sequentially illustrating an optical inspection process using the optical inspection system of FIG. 3.

Referring to FIG. 5A, the light source unit 140 may be configured to emit incident light 140*i* toward the target object 10 disposed on the supporting unit 120. In example embodiments, a laser beam may be used as the incident light 140*i*. The light source unit 140 may be configured to emit s-polarized light 140*i*. An angle of incidence θ may range from about 65° to about 85°. In example embodiments, the angle of incidence θ may range from about 70° to about 80°. This configuration may make it possible to increase reflection efficiency of the incident light 140*i* and consequently to suppress the incident light 140*i* from passing through the target object 10. By reducing the incident light 140*i* passing through the target object 10, it is possible to suppress noise from being produced by a structure disposed under the target object 10.

Figure 5B:
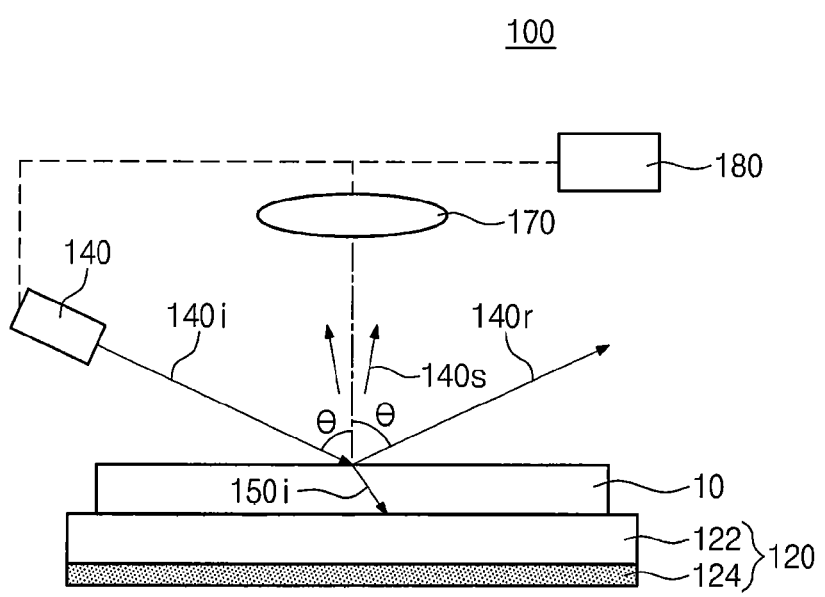

Referring to FIG. 5B, if the incident light 140*i* is irradiated on the target object 10, a fraction of the incident light 140*i* may be reflected from the target object 10 to form reflected light 140*r*. Here, another fraction of the incident light 14*i* may be firstly scattered by the target object 10 to form first scattered light 140*s*. The light condensing unit 170 may be provided over the target object 10 to collect the first scattered light 140*s*. The light condensing unit 170 may transmit image information obtained from the first scattered light 140*s* to the control unit 180. In the control unit 180, the image information may be used to examine whether there is a pollutant on the target object 10. Furthermore, the control unit 180 may examine sizes and/or positions of pollutants, which may occur on the target object 10. Here, other fraction of the incident light 140*i* may be refracted through a top surface of the target object 10 to form first refracted light 150*i* propagating into the target object 10.

Figure 5C:
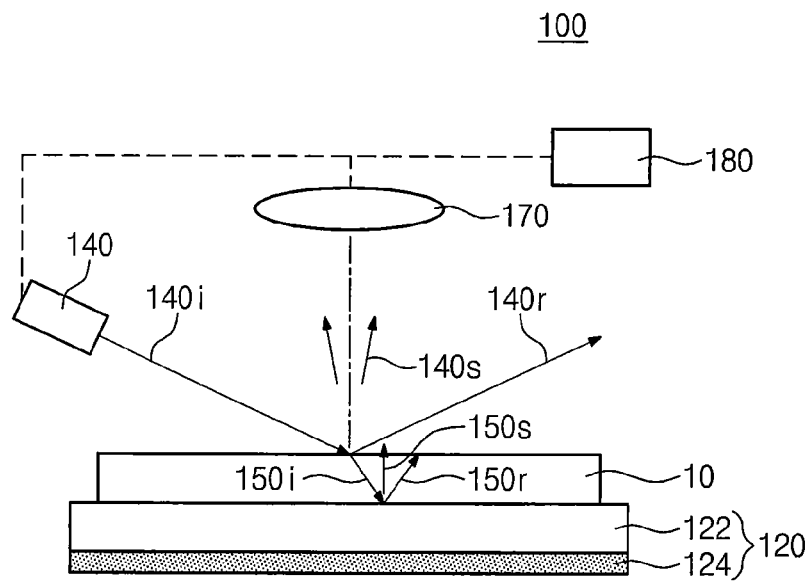

Referring to FIG. 5C, the first refracted light 150*i* may be reflected and secondly scattered by a top surface of the first supporting unit 122 to form reflected light 150*r* and second scattered light 150*s*. Since the first supporting unit 122 is positioned directly under the target object 10, the second scattered light 150*s* may be directly generated from the top surface of the first supporting unit 122. Accordingly, the second scattered light 150*s* may be incident into and be detected by the light condensing unit 170 and may serve as a noise factor in detection of pollutants based on the analysis of the first scattered light 140*s*. Here, the first supporting unit 122 may be formed of a material whose transmittance is 90% or higher, thereby allowing most of the first refracted light 150*i* to pass therethrough. This makes it possible to reduce an intensity or amount of the second scattered light 150*s*. In addition, a fraction of the first refracted light 150*i* may be refracted through the top surface of the first supporting unit 122 to form second refracted light 160*i* propagating into the first supporting unit 122.

Figure 5D:
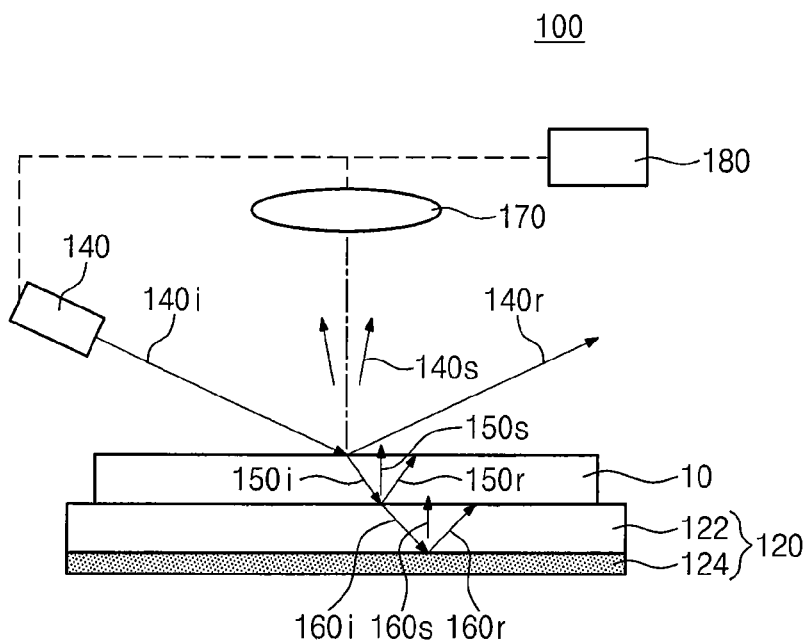

Referring to FIG. 5D, the second refracted light 160*i* may be reflected and thirdly scattered by a top surface of the second supporting unit 124 to form reflected light 160*r* and third scattered light 160*s*. The third scattered light 160*s* may be incident into the light condensing unit 170, thereby serving as a noise factor in detection of pollutants based on the analysis of the first scattered light 140*s*. Here, the second supporting unit 124 may be formed of a material with high reflectance to reflect most of the refracted light 150*i*. This makes it possible to reduce an intensity or amount of the third scattered light 160*s*.

Referring to FIGS. 3 and 5A through 5D, the optical inspection system 100 according to example embodiments of the inventive concept may be configured to control the intensities or amounts of the second scattered light 150*s* and the third scattered light 160*s*, which may serve as a noise factor in the optical inspection process to be performed based on the analysis of the first scattered light 140*s*. In other words, it is possible to finely control such undesired scattered light, and this makes it possible to detect nano-sized particles.

Figure 6:
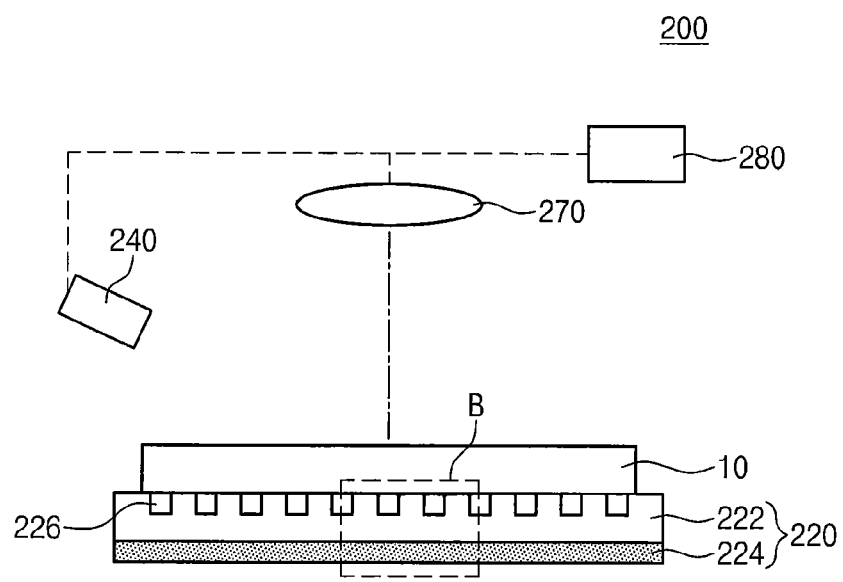
FIG. 6 is a schematic diagram illustrating an optical inspection system according to second embodiments of the inventive concept.
Figure 7:
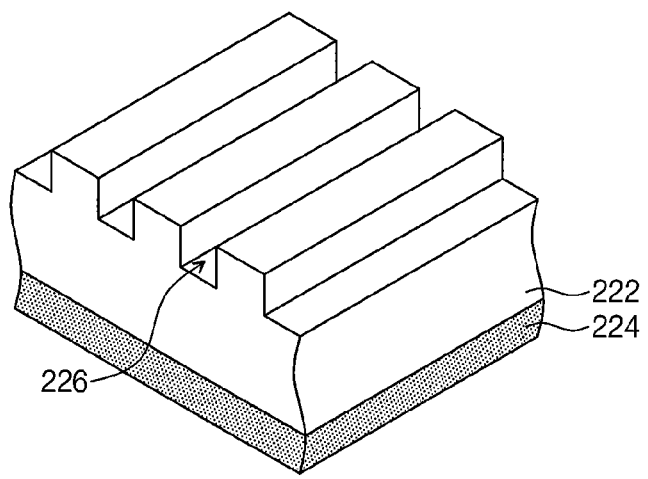
FIG. 7 is a perspective view illustrating a portion B of FIG. 6.

FIG. 6 is a schematic diagram illustrating an optical inspection system 200 according to second embodiments of the inventive concept. FIG. 7 is a perspective view illustrating a portion B of FIG. 6. The optical inspection system 200 may include a supporting unit 220, a light source unit 240, a light condensing unit 270, and a control unit 280. In the optical inspection system 200 of FIG. 6, each of the supporting unit 220, the light source unit 240, the light condensing unit 270, and the control unit 280 may be configured to have substantially the same shape or function as a corresponding one of the supporting unit 120, the light source unit 140, the light source unit 140, the light condensing unit 170, and the control unit 180 of FIG. 3. The supporting unit 220 of FIG. 6 may include a first supporting member or unit 222 and a second supporting member or unit 224. Each of the first supporting unit 222 and the second supporting unit 224 of FIG. 6 may be configured to have substantially the same shape or function as a corresponding one of the first supporting unit 122 and the second supporting unit 124 of FIG. 3. However, the first supporting unit 222 of FIG. 6 may be provided in such a way that a top surface has at least one recessed region 226. As shown in FIGS. 6 and 7, the recessed region 226 may be formed to extend from a top surface of the first supporting unit 222 toward a bottom surface of the first supporting unit 222. The recessed region 226 may be formed to have a side surface perpendicular to the top surface of the first supporting unit 222. Alternatively, the recessed region 226 may be formed to have a side surface inclined to the top surface of the first supporting unit 222. The first supporting unit 222 may be provided to have a plurality of recessed regions 226. Each of the recessed regions 226 may be provided to have a bar-shaped structure. For example, the recessed region 226 may extend in a longitudinal direction of the first supporting unit 222 to have a bar-shaped structure. In other example embodiments, the shape of the recessed region 226 may be variously changed. In certain embodiments, a plurality of the recessed regions 226 may be formed spaced apart from each other by the same distance. Due to the presence of the recessed region 226, it is possible to reduce an area of the first supporting unit 222 in direct contact with the target object 10. Accordingly, it is possible to decrease an external force (e.g., a frictional force) exerting on the target object 10, which may occur when the target object 10 is loaded or unloaded on the first supporting unit 222. In particular, in the case where the target object 10 and the first supporting unit 222 are formed of the same or similar material, the recessed region 226 may contribute to reduce technical issues, which may be caused by an external force (e.g., a frictional force). Alternatively, the second supporting unit 224 may be grounded to prevent a short circuit from being formed.

Figure 8:
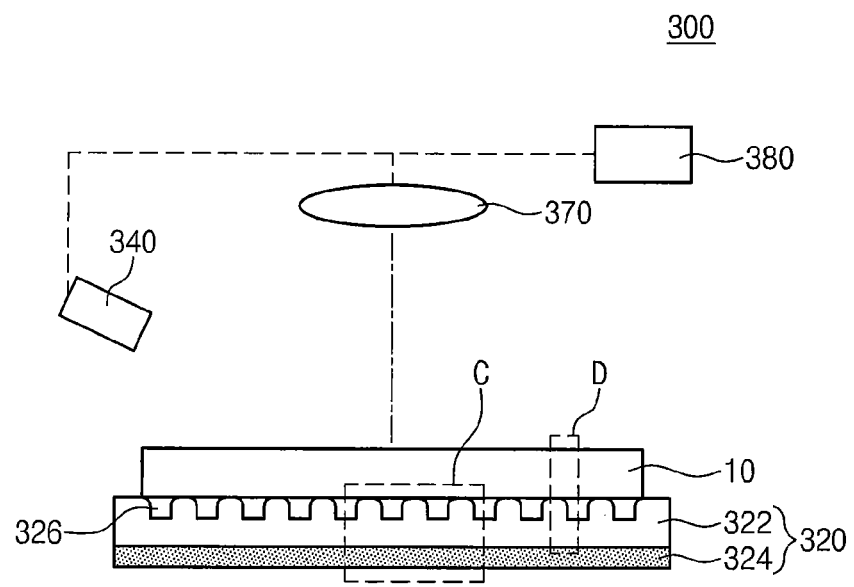
FIG. 8 is a schematic diagram illustrating an optical inspection system according to third embodiments of the inventive concept.
Figure 9:
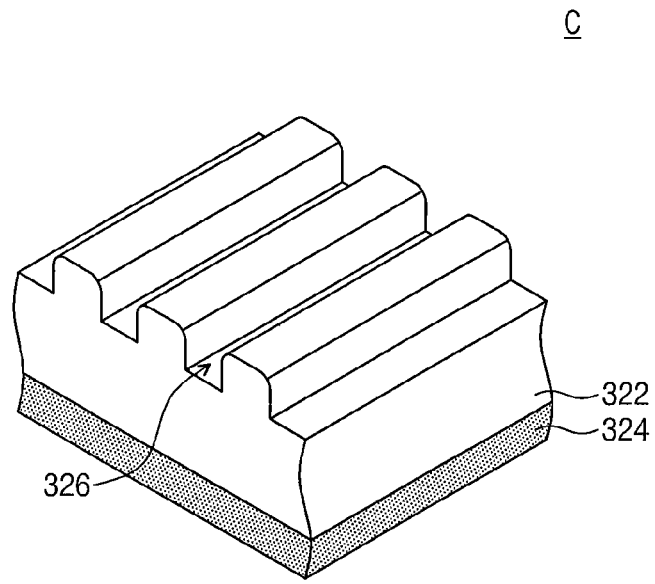
FIG. 9 is a perspective view illustrating a portion C of FIG. 8.
Figure 10:
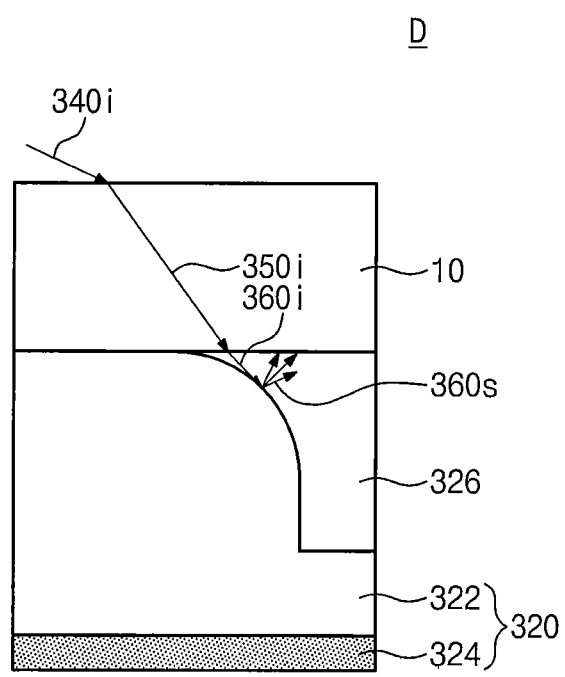
FIG. 10 is a perspective view illustrating a portion D of FIG. 8.

FIG. 8 is a schematic diagram illustrating an optical inspection system 300 according to third embodiments of the inventive concept. FIG. 9 is a perspective view illustrating a portion C of FIG. 8. FIG. 10 is a perspective view illustrating a portion D of FIG. 8. Referring to FIGS. 8 through 10, the optical inspection system 300 may include a supporting unit 320, a light source unit 340, a light condensing unit 370, and a control unit 380. In the optical inspection system 300 of FIG. 8, each of the supporting unit 320, the light source unit 340, the light condensing unit 370, and the control unit 380 may be configured to have substantially the same shape or function as a corresponding one of the supporting unit 220, the light source unit 240, the light condensing unit 270, and the control unit 280 of FIG. 6. The supporting unit 320 of FIG. 8 may include a first supporting member or unit 322 and a second supporting member or unit 324. Each of the first supporting unit 322 and the second supporting unit 324 of FIG. 8 may be configured to have substantially the same shape or function as a corresponding one of the first supporting unit 222 and the second supporting unit 224 of FIG. 6. Alternatively, the second supporting unit 324 may be grounded to prevent a short circuit from being formed.

The first supporting unit 322 may be provided in such a way that a top surface thereof has at least one recessed region 326. The recessed region 326 may be formed to extend from a top surface of the first supporting unit 322 toward a bottom surface of the first supporting unit 322. However, as shown in FIG. 8, an upper portion of the recessed region 326 may have a rounded profile. In the case where, as shown in FIG. 6, the recessed region 226 is formed to have a vertical side surface, a surface of the recessed region 226 may serve as a main cause of undesired light scattering. By contrast, in the case where, as shown in FIG. 10, the recessed region 326 is formed to have a rounded profile, a second scattered light 360*s* may be weakly produced at the surface of the recessed region 326. A fraction of incident light 340*i* may be refracted through the target object 10 to form first refracted light 350*i*, and a fraction of the first refracted light 350*i* may form second refracted light 360*i* that is incident into the air. Here, due to the rounded profile of the recessed region 326, an intensity of the second scattered light 360*s* produced from the second refracted light 360*i* may be decreased. The more gentle the rounded profile of the recessed region 326, the weaker the intensity of the second scattered light 360*s*. In other words, the rounded profile of the recessed region 326 may contribute to reduce noise caused by the second scattered light 360*s*. Due to the presence of the recessed region 326, it is possible to reduce an area of the first supporting unit 322 in contact with the target object 10. Accordingly, it is possible to decrease an external force (e.g., a frictional force) exerting on the target object 10, which may occur when the target object 10 is loaded or unloaded on the first supporting unit 322. In particular, in the case where the target object 10 and the first supporting unit 322 are formed of the same or similar material, the recessed region 326 may contribute to reduce technical issues, which may be caused by an external force (e.g., a frictional force).

Figure 11:
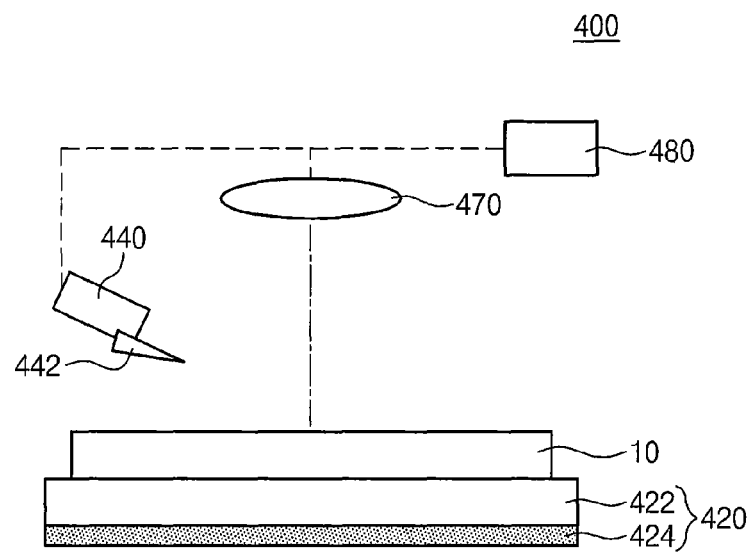
FIG. 11 is a schematic diagram illustrating an optical inspection system according to fourth embodiments of the inventive concept.

FIG. 11 is a schematic diagram illustrating an optical inspection system 400 according to fourth embodiments of the inventive concept. The optical inspection system 400 may include a supporting unit 420, a light source unit 440, a light condensing unit 470, and a control unit 480. In the optical inspection system 400 of FIG. 11, the supporting unit 420, the light source unit 440, the light condensing unit 470, and the control unit 480 may be configured to have substantially the same shape or function as a corresponding one of the supporting unit 120, the light source unit 140, the light condensing unit 170, and the control unit 180 of FIG. 3. The light source unit 440 of FIG. 11 may further include a refraction plate 442. The refraction plate 442 may be provided under the light source unit 440. The refraction plate 442 may be configured to have a thickness decreasing in a direction away from the light source unit 440. Alternatively, the refraction plate 442 may be provided in the form of a plate. The refraction plate 442 may be configured to be detachable to the light source unit 440. Furthermore, the refraction plate 442 may be configured to have an adjustable angle with respect to the light source unit 440. The refraction plate 442 may be configured to control an irradiation position A and a resulting scattering position of the laser beam.

Figure 12:
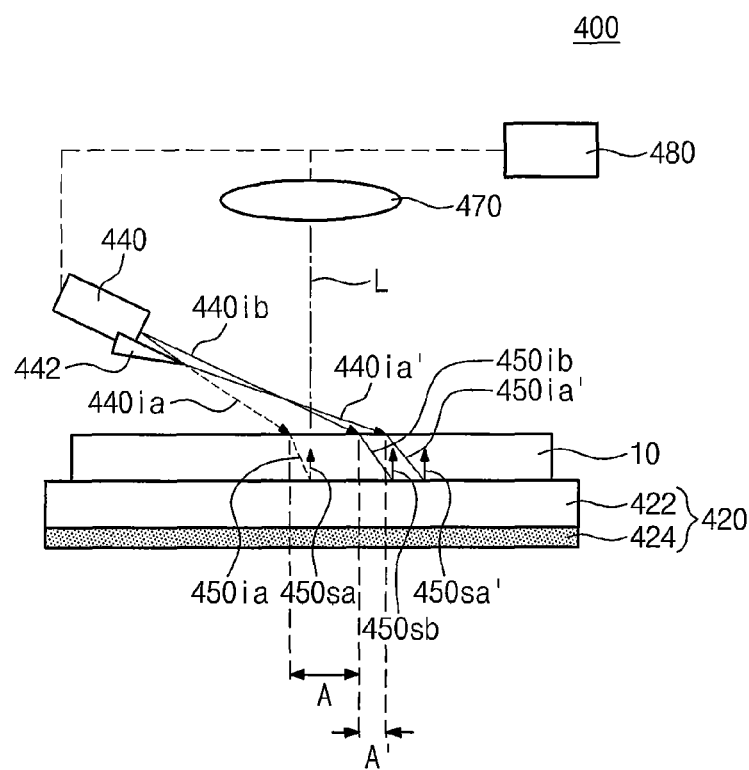
FIG. 12 is a schematic diagram exemplarily illustrating a method of controlling an irradiation position using a refraction plate of the optical inspection system of FIG. 11.

FIG. 12 is a schematic diagram exemplarily illustrating a method of controlling an irradiation position A using the refraction plate 442 of the optical inspection system 400 of FIG. 11. The light source unit 440 may be configured to emit first incident light 440$ia$ or second incident light 440$ib$. Here, the irradiation position A may be a region to which the first incident light 440$ia$ or the second incident light 440$ib$ is incident. The light source unit 440 may be configured in such a way that the first incident light 440$ia$ and the second incident light 440$ib$ are respectively incident to both edges of the irradiation position A with respect to the target object 10.

In the case where the refraction plate 442 is not provided, each of the first incident light 440$ia$ and the second incident light 440$ib$ may be reflected by and refracted through the top surface of the target object 10. Here, a first scattering may occur at the top surface of the target object 10, and first scattered light may be collected by the light condensing unit 470 and may be used to examine whether there are pollutants on the target object 10. A fraction of each of the first incident light 440$ia$ and the second incident light 440$ib$ may be refracted to incident into the target object 10. Each of the refracted lights 450$ia$ and 450$ib$ may be secondly scattered by a top surface of the first supporting unit 422. Here, by adjusting the irradiation position A of the incident lights 440$ia$ and 440$ib$, it is possible to control a noise caused by the second scattered lights 450$sa$ and 450$sb$.

In detail, if the second scattered lights 450$sa$ and 450$sb$ are generated at regions adjacent to an optic axis L of the light condensing unit 470, the noise caused by the second scattered light 450$sa$ may be abruptly increased. In this case, by using the refraction plate 442, it is possible for the incident lights 450$ia$ and 450$ib$ to be incident into a new irradiation position A'. For example, the refraction plate 442 may be configured to change a propagating direction of the first incident light 440$ia$, and thus, it can be used to change irradiation position A' of first incident light 450$ia'$. For example, the refraction plate 442 may be controlled in such a way that second scattered lights 450$sa'$ and 450$sb$ are scattered at positions spaced apart from the optic axis L. Similarly, for the third scattering on the top surface of the second supporting unit 424, if such a scattering occurs at a position on adjacent the optic axis L, the refraction plate 442 may be used to control the irradiation position A'. By changing the irradiation position A in such a way that a scattering position is spaced far from the optic axis L, it is possible to reduce the noise in the optical inspection process. Furthermore, in the case where the laser beam has a beam size larger than a predetermined width, the refraction plate 442 may be used to change the beam size (e.g., width) of the laser beam.

In FIG. 11, the supporting unit 420 is illustrated to include the first supporting unit 422 shaped like a plate, like the first supporting unit 222 of FIG. 3, but as shown in FIGS. 6 and 8, the first supporting unit 422 may be configured to have at least one recessed region 226.

Figure 13:
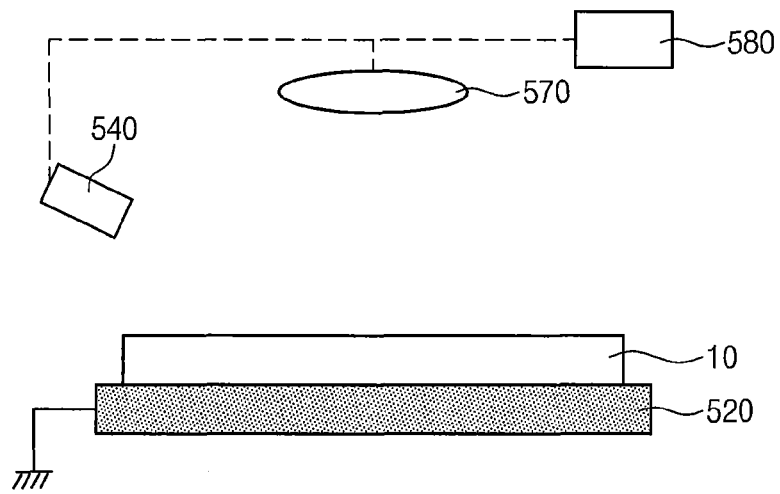
FIG. 13 is a schematic diagram illustrating an optical inspection system according to fifth embodiments of the inventive concept.

FIG. 13 is a schematic diagram illustrating an optical inspection system 500 according to fifth embodiments of the inventive concept. The optical inspection system 500 may include a supporting unit 520, a light source unit 540, a light condensing unit 570, and a control unit 580. In the optical inspection system 500 of FIG. 13, each of the light source unit 540, the light condensing unit 570, and the control unit 580 may be configured to have substantially the same shape or function as a corresponding one of the light source unit 140, the light condensing unit 170, and the control unit 180 of FIG. 3. However, the supporting unit 520 of the optical inspection system 500 may be formed of a material with high reflectance. The supporting unit 520 may be coated with a material with high reflectance. The supporting unit 520 may be a metal layer, which is treated to have a mirror effect or a mirror. Accordingly, the incident light passing through the target object 10 may be reflected by the top surface of the supporting unit 520, and thus, it is possible to reduce a noise in the optical inspection process. Here, the supporting unit 520 may be grounded to prevent a short circuit from being formed. This may make it possible to prevent an electrostatic discharging from occurring between the target object 10 and the supporting unit 520.

Figure 14:
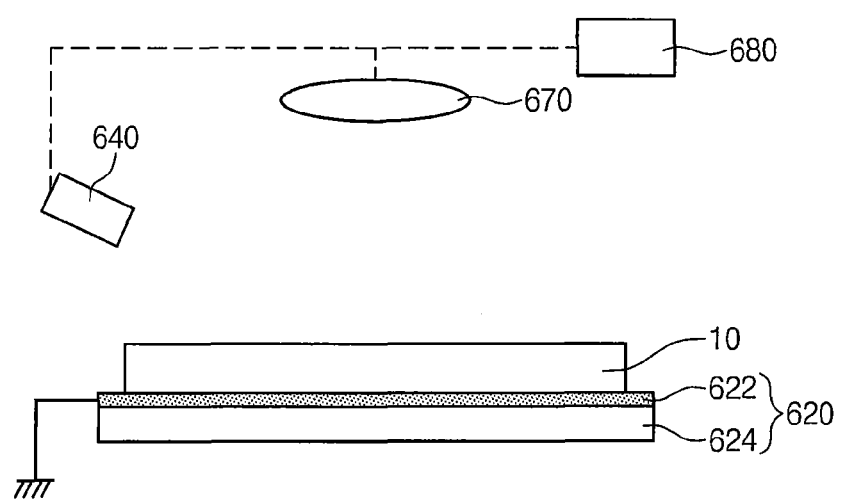
FIG. 14 is a schematic diagram illustrating an optical inspection system according to sixth embodiments of the inventive concept.

FIG. 14 is a schematic diagram illustrating an optical inspection system 600 according to sixth embodiments of the inventive concept. The optical inspection system 600 may include a supporting unit 620, a light source unit 640, a light condensing unit 670, and a control unit 680. In the optical inspection system 600 of FIG. 14, each of the light source unit 640, the light condensing unit 670, and the control unit 680 may be configured to have substantially the same shape or function as a corresponding one of the light source unit 140, the light condensing unit 170, and the control unit 180 of FIG. 3. The supporting unit 620 of the optical inspection system 600 may include a first supporting member or unit 622 and a second supporting member or unit 624. The target object 10 may be disposed on a top surface of the first supporting unit 622. The first supporting unit 622 may be formed of a material with high reflectance. The first supporting unit 622 may be a metal layer, which is treated to have a mirror effect or a mirror. Accordingly, the incident light passing through the target object 10 may be reflected by the top surface of the first supporting unit 622, and thus, it is possible to reduce a noise in the optical inspection process. The second supporting unit 624 may be disposed below the first supporting unit 622. Alternatively, the first supporting unit 622 may be a part of the second supporting unit 624 having a surface coated with a material with high reflectance. As an example, the first supporting unit 622 may be a portion of the second supporting unit 624 whose surface is treated to have a mirror effect. The first supporting unit 622 may be grounded to prevent a short circuit from being formed. This may make it possible to prevent an electrostatic discharging from occurring between the target object 10 and the first supporting unit 622.

According to example embodiments of the inventive concept, it is possible to fabricate a highly reliable optical inspection system.

According to example embodiments of the inventive concept, it is possible to fabricate an optical inspection system configured to reduce a noise, which may be caused by other scattered light other than desired scattered light.

While example embodiments of the inventive concepts have been particularly shown and described, it will be understood by one of ordinary skill in the art that variations in form and detail may be made therein without departing from the spirit and scope of the attached claims.

What is claimed is:

1. An optical inspection system, comprising:
   a supporting unit;
   a light source unit configured to emit a laser beam toward a target object on the supporting unit;
   a light condensing unit configured to collect scattered light when the target object is irradiated with the laser beam; and
   a control unit configured to control the light source unit and the light condensing unit and to analyze the scattered light to determine if pollutants are on the target object,
   wherein the supporting unit comprises:
      a first supporting member, on which the target object is disposed, and which comprises a first material; and
      a second supporting member under the first supporting member, wherein the second supporting member comprises a second material different from the first material,
      wherein the first material has a higher light transmittance than the second material, and
      wherein the second material has a higher light reflectance than the first material.

2. The system of claim 1, wherein the light transmittance of the first material is at least 90%.

3. The system of claim 1, wherein the second material comprises a metal layer-treated to have a mirror effect.

4. The system of claim 1, wherein the control unit is configured to control a position of the light source unit such that an incidence angle of the laser beam ranges from about 70° to about 80°.

5. The system of claim 1, wherein the target object comprises a transparent substrate.

6. The system of claim 1, wherein the first supporting member comprises at least one recessed region having a bottom surface that is lower than a top surface of the first supporting member.

7. The system of claim 6, wherein an upper portion of the at least one recessed region has a rounded profile.

8. The system of claim 1, wherein the light source unit further comprises a refraction plate configured to control an irradiation position of the laser beam.

9. The system of claim 1, wherein the light source unit is configured to generate an s-polarized laser beam.

10. An optical inspection system, comprising:
    a supporting unit;
    a light source unit configured to emit a laser beam toward a target object on the supporting unit;
    a light condensing unit configured to collect scattered light when the target object is irradiated with the laser beam; and
    a control unit configured to control the light source unit and the light condensing unit and to analyze the scattered light to determine if pollutants are on the target object,
    wherein the supporting unit comprises:
       a first supporting member, on which the target object is disposed, and which comprises a first material; and
       a second supporting member under the first supporting member, wherein the second supporting member comprises a second material different from the first material,
       wherein the first supporting member comprises at least one recessed region extending from a top surface of the first supporting member toward a bottom surface of the first supporting member,
       wherein the first material has a higher light transmittance than the second material, and
       wherein the second material has a higher light reflectance than the first material.

11. The system of claim 10, wherein an upper portion of the at least one recessed region has a rounded profile.

12. The system of claim 10, wherein the first supporting member further comprises at least one protruding region defined by a pair of the recessed regions, the at least one protruding region having a bar-shaped structure.

13. The system of claim 12, wherein the target object directly contacts the at least one protruding region.

14. The system of claim 10, wherein a plurality of the recessed regions are spaced apart from each other by a same distance.

15. An optical inspection system, comprising:
    a supporting unit;
    a light source unit configured to emit a laser beam toward a target object on the supporting unit;
    a light condensing unit configured to collect scattered light when the target object is irradiated with the laser beam; and
    a control unit configured to control the light source unit and the light condensing unit and to analyze the scattered light to determine if pollutants are on the target object,
    wherein the supporting unit is grounded,
    wherein the supporting unit comprises first and second supporting members, wherein the target object is on a top surface of the first supporting member, and
    wherein the top surface of the first supporting member comprises a metal layer treated to have a mirror effect.

16. The system of claim 15, wherein the target object comprises a transparent substrate.

17. The system of claim 15, wherein the first supporting member of the supporting unit is grounded.

* * * * *

UNITED STATES PATENT AND TRADEMARK OFFICE
CERTIFICATE OF CORRECTION

PATENT NO. : 10,006,872 B2
APPLICATION NO. : 14/955331
DATED : June 26, 2018
INVENTOR(S) : Wonguk Seo et al.

Page 1 of 1

It is certified that error appears in the above-identified patent and that said Letters Patent is hereby corrected as shown below:

On the Title Page

Item (73), Assignee, please correct:
"Samsung Electronics Co., Ltd. (KR)"

To read:
-- Samsung Electronics Co, Ltd. (KR);
Samsung Display Co., Ltd. (KR) --

Signed and Sealed this
Twentieth Day of October, 2020

Andrei Iancu
*Director of the United States Patent and Trademark Office*